United States Patent [19]

Sekikawa et al.

[11] Patent Number: 5,198,335
[45] Date of Patent: Mar. 30, 1993

[54] INTEGRAL MULTILAYER ANALYTICAL ELEMENT FOR ANALYSIS OF AMMONIA-FORMING SUBSTRATE

[75] Inventors: Nobuyoshi Sekikawa; Harumi Katsuyama; Asaji Kondo, all of Asaka, Japan

[73] Assignee: Fuji Photo Film Co., Ltd., Kanagawa, Japan

[21] Appl. No.: 608,014

[22] Filed: Oct. 31, 1990

Related U.S. Application Data

[63] Continuation of Ser. No. 251,933, Sep. 28, 1988, abandoned, which is a continuation of Ser. No. 870,242, Jun. 3, 1986, abandoned.

[30] Foreign Application Priority Data

Jun. 4, 1985 [JP] Japan .................. 60-122348

[51] Int. Cl.$^5$ .......... C12Q 1/00; C12Q 1/32; G01N 33/52
[52] U.S. Cl. .......... 435/4; 422/56; 435/26; 436/116; 436/170; 436/175
[58] Field of Search .......... 435/4, 18, 22, 26, 12, 435/805; 436/175, 113, 169, 170; 422/56-58

[56] References Cited

U.S. PATENT DOCUMENTS

| | | | |
|---|---|---|---|
| 4,066,403 | 1/1978 | Bruschi .......... | 436/108 X |
| 4,303,408 | 12/1981 | Kim et al. .......... | 422/57 X |
| 4,548,906 | 10/1985 | Sekikawa et al. .......... | 422/58 X |
| 4,719,085 | 1/1988 | Jacobs .......... | 436/113 X |

FOREIGN PATENT DOCUMENTS 0044865 3/1985 Japan .................. 436/113

OTHER PUBLICATIONS

Amano et al., Chemical Abstracts, vol. 101, 1984, No. 101:3544v.
Cambiaghi et al., Chemical Abstracts, vol. 98, 1983, 98:103928m.
Mascini et al., Chemical Abstracts, vol. 103, 1985, No. 103:67134k.
Oriental I, Chemical Abstracts, vol. 100, 1984, No. 100:153452g.
Oriental II, Chemical Abstracts, vol. 100, 1984, No. 100:188432c.
Oriental III, Chemical Abstracts, vol. 100, 1984, No. 100:188433d.
Mascini, et al., Analytica Chimica Acta, 171 (1985) pp. 175-184.

*Primary Examiner*—Jill A. Johnston
*Attorney, Agent, or Firm*—McAulay Fisher Nissen Goldberg & Kiel

[57] ABSTRACT

An integral multilayer analytical element for the analysis of an ammonia-forming substrate comprising:
(I) a light-transmissive, liquid-impermeable support:
(II) an ammonia indicator layer containing a reagent capable of undergoing a detectable change by gaseous ammonia;
(III) a liquid barrier layer which allows gaseous ammonia passing therethrough;
(IV) an ammonia-forming substrate reaction layer containing a reagent capable of reacting with an ammonia-forming substrate to form gaseous ammonia;
(V) an intrinsic ammonia trapping layer containing a reagent which acts on intrinsic ammonia to convert it into a form which can not reach said reaction layer; and
(IV) a porous spreading layer, in a laminate form.

7 Claims, 1 Drawing Sheet

FIG. 1

INTEGRAL MULTILAYER ANALYTICAL ELEMENT FOR ANALYSIS OF AMMONIA-FORMING SUBSTRATE

This a continuation of application Ser. No. 251,933, filed Sep. 28, 1988, now abandoned, which, in turn, is a continuation of application Ser. No. 870,242, filed Jun. 3, 1986 now abandoned.

BACKGROUND OF THE INVENTION

1. Field of the Invention

The present invention relates to an integral multilayer analytical element for use in the analysis of an ammonia-forming substrate in liquid samples, and more particularly to an integral multilayer analytical element suitable for use in the analysis (assay) of an ammonia-forming substrate, such as, creatinine, urea, etc., in body fluids, such as, blood, urine, lymph fluid, etc. without being affected by intrinsic ammonia.

2. Description of Prior Arts

The assaying of ammonia-forming substrates, such as, creatinine, urea, etc., is very important in the diagnosis of diseases, such as renopathy, the inspection of the progress of diseases and the inspection of the function of kidney.

A typical method for analyzing ammonia-forming substrates is a method comprising forming ammonia from the substrates and determining the amount of formed ammonia. This analytical method utilizing the conversion of the substrates into ammonia has been widely used as a method which is generally called a wet process or a solution method.

In the above operation for forming ammonia from the ammonia-forming substrates, method usually used is forming ammonia by the action of an enzyme. For instance, in the analysis of creatinine in body fluids, a method is utilized in which creatinine in the body fluids is specifically hydrolyzed into ammonia and N-methyl hydantoin by using creatinine deiminase (EC 3.5.4.21). In the analysis of blood urea nitrogen (hereinafter referred to as BUN), a method is used in which urea is hydrolyzed into ammonia and carbon dioxide by using urease as a catalyst.

For determining the amount of ammonia formed, various methods known as ammonia-assaying methods can be used. For instance, a method in which the formed an ammonia is determined by means of ammonia ion-selective electrode, and a method in which the color of a pH indicator is changed by the ammonia formed and the degree of color change is measured to thereby determine the amount of ammonia are used. Also used is a method in which the formed ammonia is coupled with α-ketoglutaric acid in the presence of glutamate dehydrogenase (EC 1.4.1.3) and NADH (nicotinamide adenine dinucleotide of the reduced type) to form L-glutamic acid and water. The amount of $NAD^+$ (nicotinamide adenine dinucleotide of the oxidized type) to be formed or the amount of NADH to be reduced by the conversion of NADH into $NAD^+$ is determined by means of fluorometry or photometry utilizing near-ultraviolet light at a wavelength of 340 nm. Another method is used in which NADPH (nicotinamide adenine dinucleotide phosphate of the reduced type) is used in place of said NADH, and the amount of $NADP^+$ (nicotinamide adenine dinucleotide phosphate of oxidized type) to be formed or the amount of NADPH to be reduced by the conversion of NADPH into $NADP^+$ is determined.

The analytical methods for the ammonia-forming substrates comprising the aforementioned two operations are described in literature, such as, Analytical Chemistry, 46, 246(1974); Clinica Chemica Acta, 18, 409(1967); Clinical Chemical Analysis III Nitrogen-containing Component (written in Japanese), the second edition, pages 13–14 and 67–87 (1979) (Tokyo Kagaku Dojin Ltd., Japan); and Clinical Inspection, Vol. 5, No. 6, pages 387–391 (1961) written in Japanese.

Ammonia (intrinsic ammonia) is frequently present as ammonium ion in the free form in body fluids to be analyzed, and the error caused by the intrinsic ammonia is non-negligible. Accordingly, it is necessary to eliminate the influence of the intrinsic ammonia on the accurate determination of the ammonia forming substrates, and methods have been proposed for removing intrinsic ammonia.

An example of an analytical method for ammonia forming substrates including an operation for previously removing intrinsic ammonia is an automatic continuous flowing method for creatinine analyte disclosed in Japanese Patent Provisional Publication No. 58(1983)-5198 in which an operation comprising reacting a sample with a reagent (e.g., a reagent consisting of glutamate dehydrogenase, α-ketoglutamic acid and NADH) capable of removing intrinsic ammonia and dialyzing any unreacted creatinine contained in the reaction mixture by a dialyzer is carried out as a pre-step in an operation for forming ammonia from creatinine.

Methods for pretreating an analyte are disclosed in Japanese Patent Provisional Publication Nos. 59(1984)-21398 and 59(1984)-31689 comprising using NADP reductase (or NAD reductase), restoring $NADP^+$ (or $NAD^+$) formed as a by-product to the original NADPH (or NADH) and recycling for use in a method for eliminating intrinsic ammonia by reacting NADPH (or NADH), glutamate dehydrogenase and α-ketoglutamic acid with the intrinsic ammonia. In the analysis of the ammonia-forming substrates by using said pretreating method, an enzyme capable of forming ammonia from the substrate is added to the pretreated analyte and the formed ammonia is determined by using a reagent system comprising NADH (or NADPH), glutamate dehydrogenase and α-ketoglutamic acid as described in Japanese Patent Provisional Publication Nos. 59(1984)-31696, 59(1984)-31698 and 59(1984)-31700.

The above-described analytical methods have been carried out by methods conventionally called wet process or a solution method, or they have been proposed with a view to conducting a wet process. Nevertheless, an analytical method which can be performed with only a small amount of a sample and can be easily operated with high accuracy, has been highly desired by medical persons, such as, medical doctors in clinical tests. Therefore, dry analytical methods which are easy to handle, are now used in place of the conventional wet analytical methods. As an analytical element for the ammonia-forming substrate in the dry analytical method, a test piece for the analysis of blood urea nitrogen (BUN) is disclosed in U.S. Pat. No. 3,011,874. Further, analytical methods have been developed analytical methods using an integral multilayer analytical element (hereinafter referred to simply as analytical element)

which can be easily operated with high accuracy, and the improvements in the element are being made.

Examples of integral multilayer analytical elements which can be used for the analysis of the ammonia-forming substrates include the element disclosed in Japanese Patent Publication No. 58(1983)-19062 and the elements for the analysis of ammonia or the ammonia-forming substrate described in Japanese Patent Provisional Publication Nos. 58(1983)-77660 and 58(1983)-77661. These analytical elements comprise basically laminating an ammonia indicator layer capable of undergoing a detectable change by contact with ammonia, a barrier layer which functions as a liquid barrier and allows gaseous ammonia to be passed therethrough, a reaction layer containing a reagent capable of forming ammonia by the reaction with an ammonia-forming substrate and a porous spreading layer in this order onto a liquid-impermeable, light-transmissive support. However, these analytical elements can not eliminate the influence of ammonia (intrinsic ammonia) present in body fluids. Accordingly, it is difficult to determine accurately the ammonia-forming substrate by these analytical elements.

The method for removing intrinsic ammonia described in the aforementioned Japanese Patent Provisional Publication No. 58(1983)-5198, which must use a dialysis device for discharging a product of the reaction between a reagent and intrinsic ammonia to the outside of the reaction system, is generally applied to a wet analytical method and cannot be used, as, such for the dry analytical method using said integral multilayer analytical element. In the method described in the aforementioned Japanese Patent Provisional Publication No. 59(1984)-21398, complicated operations comprising reacting intrinsic ammonia, measuring the OD of a blank and adding creatinine deiminase are carried out and then creatinine is determined by a reaction for forming ammonia from creatinine.

SUMMARY OF THE INVENTION

It is an object of the present invention to eliminate error in measurement due to intrinsic ammonia in an integral multilayer analytical element for the analysis of ammonia-forming substrates.

It is another object of the invention to provide an integral multilayer analytical element which can analyze simply and rapidly, an ammonia-forming substrate, such as, creatinine or blood urea nitrogen (BUN) without requiring complicated operations.

The present invention provides an integral multilayer analytical element for the analysis of an ammonia-forming substrate, which comprises in this order:

(I) a light-transmissive, liquid-impermeable support;

(II) an ammonia indicator layer containing an indicator capable of undergoing a detectable change by gaseous ammonia;

(III) a liquid barrier layer which allows gaseous ammonia passing therethrough;

(IV) an ammonia-forming substrate reaction layer containing a reagent capable of reacting with an ammonia-forming substrate to form gaseous ammonia;

(V) an intrinsic ammonia trapping layer containing a reagent which acts on intrinsic ammonia to convert it into a form which can not reach said reaction layer; and (VI) a porous spreading layer, in a laminate form. In the element, layer (I) is the lowermost member and layer (VI) is the uppermost layer.

If desired, the analytical element of the invention may be provided with other known functional layers, such as, known intermediate layer, an adhesive layer and a light-blocking layer, so long as these layers do not interfere with the performance of the analytical element of the present invention.

The term "ammonia-forming substrate" used herein refers to a compound or a compound group which produces ammonia therefrom by the reaction with a specified reagent or which produces ammonia via a plurality of reaction systems.

The analytical element of the invention functions in such a manner that intrinsic ammonia is previously trapped by an upper layer (intrinsic ammonia trapping layer) to remove it, an ammonia-forming substrate such as creatinine or blood urea nitrogen (BUN) is reacted in the reaction layer, and the formed ammonia is subjected to a color reaction in the indicator layer to detect and analyze it. Accordingly, when the analytical element of the invention is used, complicated operations, such as, the determination of the amount of intrinsic ammonia, removal of intrinsic ammonia as a pretreatment and the dialysis of a sample solution are not required and hence, creatinine or urea can be determined simply and rapidly. In addition, the analytical element of the invention is in an integrated form so that it can be easily used and is easy to handle.

In the analytical element of the invention, the ammonia-forming substrate is indirectly determined by reacting the ammonia-forming substrate (analyte) with a reagent capable of forming ammonia by the reaction with said substrate and determining the amount of ammonia formed. Accordingly, the analytical element of the invention can serve as an element for the analysis of various ammonia-forming substrates by changing the type of the reagent for the formation of ammonia.

DETAILED DESCRIPTION OF THE INVENTION

The integral multilayer analytical element of the present invention has a basic structure comprising:

(I) a light-transmissive, liquid-impermeable support;

(II) an ammonia indicator layer containing a reagent capable of undergoing a detectable change by gaseous ammonia;

(III) a liquid barrier layer which allows gaseous ammonia to pass therethrough;

(IV) an ammonia-forming substrate reaction layer containing a reagent capable of reacting with an ammonia-forming substrate to form gaseous ammonia;

(V) an intrinsic ammonia trapping layer containing a reagent which acts on intrinsic ammonia to convert it into a form which can not reach said reaction layer; and (VI) a porous spreading layer.

Figure 1:
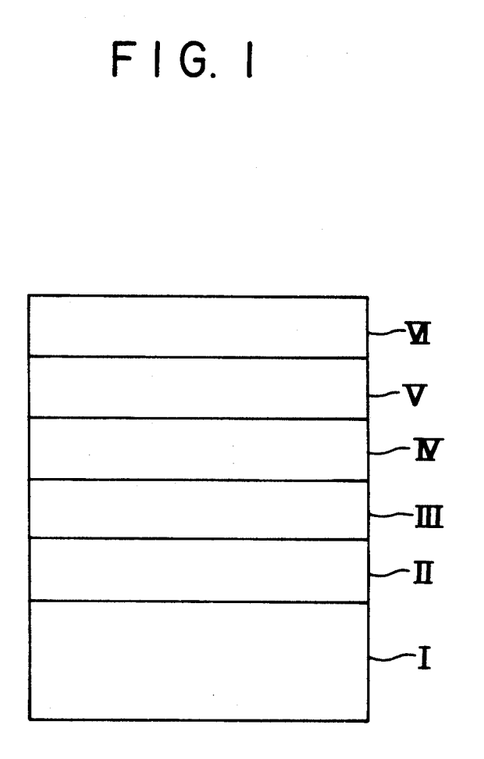
FIG. 1 shows schematically an embodiment of the basic structure of an integral multilayer analytical element of the present invention for use in the analysis of ammonia forming substrate.

FIG. 1 shows schematically an embodiment of the basic structure of an integral multilayer analytical element of the invention for use in the analysis of an ammonia forming substrate, wherein I is a light-transmissive, liquid-impermeable support, II is an ammonia indicator layer, III is a liquid barrier layer, IV is an ammonia-forming substrate reaction layer, V is an intrinsic ammonia trapping layer and VI is a porous spreading layer.

Examples of the liquid-impermeable, light-transmissive supports (hereinafter referred to as support) used in the integral multilayer analytical element of the present invention include substantially water-impermeable transparent supports made of a polymer, such as, polyethylene terephthalate, polycarbonate of bisphenol A, polystyrene and cellulose esters (e.g., cellulose diacetate, cellulose triacetate, cellulose acetate propionate etc.). The thickness of the support generally ranges from approx. 50 μm to approx. 1 mm, and preferably from approx. 80 μm to approx. 300 μm.

An undercoating layer may be provided on the support to enhance the adhesion between the support and the reaction layer or optionally added other intervening layer (e.g., absorbent layer) may be added. Instead of the undercoating layer, the surface of the support may be activated by physical or chemical process to enhance the adhesion.

On the support (optionally, with other layers, such as, an undercoating layer), there is provided the ammonia indicator layer (hereinafter referred to as the indicator layer) containing at least one indicator capable of undergoing a detectable change by contact with ammonia. The indicator, layer contains at least one color indicator for ammonia. The term "color indicator for ammonia" used herein refers to a compound which produces a detectable change (e.g., color change or color formation by change in absorption wavelength) by gaseous ammonia.

Examples of the color indicators employable in the analytical element of the invention include leuco dyes, such as, leucocyanine dyes, nitro-substituted leuco dyes and leucophthalein (see, U.S. Pat. No. Re. 30,267 and Japanese Patent Publication No. 58(1983)-19062); pH indicators, such as, Bromophenol Blue, Bromocresol Green, Bromothymol Blue, Quinoline Blue and rosolic acid (see, Encyclopaedia Chimica, Vol. 10, pp 63–65, published by Kyoritsu Shuppan K. K.); triarylmethane dye precursors; leucobenzylidene dyes (see, Japanese patent Provisional Publication Nos. 55(1980)-379 and 56(1981)-145273); diazonium salt and azo dye couplers; and base bleaching dyes.

The indicator layer is formed in such a manner that at least one of said color indicators is mixed with an organic solvent-soluble polymer binder or a water-soluble polymer binder and the resulting coating solution is applied to the surface of the transparent support and then dried. Examples of such polymer binders include cellulose esters, such as, cellulose monoacetate, cellulose diacetate, cellulose triacetate, cellulose acetate butyrate and cellulose acetate propionate; alkyl-celluloses such as methylcellulose, ethylcellulose and propylcellulose; and synthetic vinyl polymers, such as, polymethyl methacrylate, polyacrylates, polystyrene, polyacrylonitrile, polyvinyl acetate, polyvinyl butyral, chlorinated polyvinyl acetate polyacrylamide, polyvinyl pyrrolidone and polyvinyl alcohol and copolymers thereof.

Preferably, the color indicator is used in an amount of 10 to 70% by weight based on the amount of the binder. In order to inhibit the color formation or the color change of the color indicator during manufacture or preservation, an organic or inorganic acid can be added to the indicator layer, whereby the pH value of the indicator layer can be adjusted so as to keep the pH value without its color formation range. Examples of such acid include ethane-sulfonic acid, aspartic acid, azelaic acid, glutaric acid, succinic acid, glutaconic acid, tartaric acid, pimelic acid, malonic acid, malic acid, 3,3-dimethylglutaric acid, citric acid, p-toluenesulfonic acid, perchloric acid and hydrochloric acid.

The coating solution for the formation of the indicator layer can be prepared by dissolving said color indicator, said polymer binder and optionally, other reagents, such as, said pH-adjusting acid in water or an organic solvent, such as, acetone, 2-methoxyethanol, methyl ethyl ketone, dichloromethane, dichloroethane, methanol or ethanol in such a proportion as to give a solid concentration of about 1 to 20% by weight, and preferably from about 3 to 10% by weight. The coating solution is coated on the surface of the support in such an amount as to give a dry film of about 1 to 30 μm, preferably from about 2 to 20 μm in thickness, and the coated support is dried, thus forming the indicator layer on the support.

On the indicator layer, a liquid barrier layer (hereinafter referred to sometimes as barrier layer) which allows gaseous ammonia to pass therethrough. As used herein barrier layer means a layer composed of a material which is substantially impermeable to liquids, such as, coating solutions and sample solutions and inhibitors (e.g., alkaline component) present in said liquids, but allows gaseous ammonia to pass therethrough in the course of the manufacture of the analytical element (that is, during the course of the formation of a reaction layer described hereinafter by coating the barrier layer with a coating solution) and/or in the course of the analysis.

The barrier layer may be structurally classified into two embodiments. One is composed of a porous material containing open cells and is an air barrier layer in which an air layer functions as a barrier, and the other is a polymer barrier layer which is a homogeneous nonporous thin layer composed of a hydrophobic (or poorly hydrophilic) polymer.

Examples of the porous materials containing open cells which can be used for the air barrier layer include membrane filters; porous materials prepared by interlacing a fibrous material or bonding it (e.g., paper, filter paper, felt, nonwoven fabric, etc.); and porous materials composed of woven fabric, knitted fabric or fine netting.

Examples of the membrane filters which can be used as the air barrier layer include those prepared from acetate (e.g., diacetate or triacetates), cellulose nitrate, regenerated cellulose, polyamide (e.g., nylon), polycarbonate of bisphenol A, polyethylene or polypropylene. The thickness of the membrane filter is about 30 to 300 μm, preferably from about 70 to 200 μm, the void volume thereof is about 25 to 90%, preferably from 65 to 85% and the average pore size thereof is 0.01 to 20 μm, preferably from about 0.1 to 10 μm. Membrane filters having such properties can be prepared by methods described in U.S. Pat. No. 1,421,341 and Japanese Patent Publication No. 53(1978)-21677. A number of the membrane filters are commercially available and these filters can be used. Examples of such commercially available membrane filters include FM series, such as, microfilter FM 22, FM 30, FM 45, FM 55, FM 80, FM 120, FM 300 and FM 500 and FR series (Fuji Photo Film Co., Ltd.); SM 11301, SM 11103, SM 11907 and SM 13604 (Sartorius GmbH); FA, FH, LC and LS series, such as, FALP 14200 and LSWP 14200 (Millipore Corp.); Membrane Filters TM, TM-P and TM-A and Ultrafilter UH, UK and UP (Toyo Chemical Co., Ltd.); and microporous membrane Cellpore NW-01 and W-01 (Sekisui Chemical Co., Ltd.).

The porous material, in which a fibrous material is interlaced or internally bonded, which can be used as the air barrier layer is one containing open cells (continuous voids) composed of a physically interlaced fibrous material or aggregate or a chemically bonded fibrous material or aggregate.

Examples of the fibrous materials which can be used for the porous material, include natural fibrous material such as, cellulose fiber, cotton fiber, flax fiber, silk fiber and wool fiber; fibers composed of regenerated or semi-synthetic material, such as, rayon, vinylon and cellulose acetate; fibrous materials composed of a synthetic material, such as, glass wool, polyethylene fiber, polyethylene terephthalate fiber, polyacrylonitrile fiber and polyvinyl chloride fiber; and blends thereof. Examples of the porous materials prepared from the fibrous materials include Japanese paper, such as, Japanese writing paper, Mino paper and shoji paper; paper such as filter paper, parchment paper and artificial parchment; felt and nonwoven cloth.

The voids of the porous material prepared from said fibrous material are in the range from about 20 to 90%, and preferably from about 50 to 85%. The average pore size of the porous material is in the range from about 0.01 to 20 $\mu$m, and preferably about 0.1 to 10 $\mu$m, and the thickness thereof is in the range from about 50 to 500 $\mu$m, and preferably from about 70 to 300 $\mu$m.

Examples of the fabrics which can be used as the air barrier layer include fabrics composed of natural fiber (e.g., cotton broadcloth); fabrics composed of semi-synthetic fiber (e.g., broad goods composed of regenerated cellulose fiber, such as, Fortizan, viscous rayon or cuprammonium rayon); fabrics composed of synthetic fiber (e.g., broad goods composed of polyamide, such as, nylon, polyethylene terephthalate or polyacrylonitrile fiber); and mixed fabrics composed of a natural fiber and a synthetic or semi-synthetic fiber (e.g., broad goods composed of a mixed yarn of cotton fiber with polyethylene terephthalate fiber). Examples of the knitted fabrics which can be used as the air barrier layer include those composed of the same fiber as those used for the preparation of the above-described fabric or the twist yarn of said fiber. Examples of the fine nets which can be used as the air barrier layer include fine nets or fine meshes composed of a synthetic fiber or yarn (e.g., fiber or yarn of polyamide, such as, nylon, polyethylene terephthalate, polyacrylonitrile, polyethylene, polypropylene or polyvinyl chloride). The thickness of the woven fabric, the knitted fabric or the net is generally in the range from about 30 to 300 $\mu$m, and the amount of voids is in the range from about 20 to 60%, and preferably from about 40 to 50%.

It is possible that a liquid containing an inhibitor dissolved therein, and particularly an alkaline material may pass through the open cells (continuous voids) of the air barrier by capillarity action. Therefore, it is desirable that the air barrier layer is hydrophobic or water repellent to an extent such that capillary flow does not occur. Accordingly, when the porous material is insufficiently hydrophobic or water repellent, it is desirable that the material be treated to make it hydrophobic or water repellent. Such a treatment can be effected by using a conventional hydrophobicity-imparting agent or water repellency-imparting agent, such as, silicon resin, silicone oil, fluororesin or fluorine-containing oil. The agent is applied to at least one side of the porous material, or a solution (solid content of 0.1 to 5 wt.%) obtained by diluting said agent with a solvent (e.g., hexane, cyclohexane or petroleum ether) is applied to at least one side of the porous material by immersion, coating, or spraying methods.

The air barrier layer can be formed by bonding the porous material to said organic solvent-soluble or water-soluble polymer binder constituting the matrix of said indicator layer. The bonding can be made by laminating the porous material to the indicator layer which is still in a wetted state and then drying the laminate. The phrase "indicator layer still in a wetted state" means that the solvent containing the binder dissolved therein remains or that a dried film is re-wetted with a soluble solvent (organic solvent or water) and the binder constituting the matrix of the indicator layer is in a swollen, dispersed or in a dissolved state. However, when the binder is a tacky material, such as, polyvinyl acetate, the porous material can be bonded to the indicator layer by bonding the porous material as such to the indicator layer under pressure without making the indicator layer wet.

The polymer barrier layer composed of a hydrophobic (or poorly hydrophilic) polymer is preferably a homogeneous non-porous thin layer. Examples of the hydrophobic (or poorly hydrophilic) polymers include cellulose acetate propionate, cellulose acetate butyrate, polycarbonate of bisphenol A, polyethylene, polypropylene, ethylene-vinyl acetate copolymer, polyurethane, polystyrene, polyvinyl chloride, vinyl chloride-vinyl acetate copolymer, polyamide (nylon), polymethyl methacrylate and polyvinyl butyral, such polymers may be used either alone or as a mixture of two or more of them.

The thickness of the polymer barrier layer is in the range of about 0.1 to 6 $\mu$m, preferably about 0.2 to 3 $\mu$m. The polymer barrier layer can be provided by coating an organic solvent solution of said polymer and drying it by any of methods described in Japanese Patent Publication No. 58(1983)-19062 and Japanese Patent Provisional Publication No. 60(1985)-21452.

The air barrier layer composed of a membrane filter or a water repellent-treated membrane filter is preferred as the barrier layer from the viewpoints of the shortness of the analytical time, high sensitivity and evenness in the color formation or the color change of the indicator layer.

A the reaction layer containing a reagent capable of reacting with the ammonia-forming substrate to form ammonia (hereinafter referred to sometimes as reaction layer) is provided directly on said barrier layer, or intervened by a tacky intermediate layer described hereinafter. The reaction layer is preferably a layer which contains a reagent (usually, enzyme or a reagent containing an enzyme) capable of reacting with the ammonia-forming substrate, an alkaline buffering agent for efficiently liberating ammonia formed by the reaction as gaseous ammonia and a film-forming hydrophilic polymer binder.

Preferably, the reagent capable of reacting with the ammonia-forming substrate to form ammonia is enzyme or a reagent containing an enzyme. An enzyme suitable for analysis can be chosen according to the type of the ammonia-forming substrate used as the analyte. When an enzyme is used as the reagent, the combinations of the ammonia-forming substrate and the reagent include urea/urease, creatinine/creatinine deiminase, amino acid/amino acid dehydrogenase, amino acid/amino acid oxidase, amino acid/ammonialyase, amine/amine oxidase, glucose and phosphoamidate/phosphoamidate hexose phosphotransferase, ADP/carbamate kinase and carbamoyl phosphate, acid amide/amidohydrolases, nucleo base/nucleo base deaminase, nucleoside/nucleoside deaminase, nucleotide/nucleotide deaminase and guanine/guanase.

Examples of the alkaline buffering agents which can be used in the reaction layer are those having a pH of 7.0 to 10.5, preferably 7.5 to 10.0. Examples of the buffering agents include ethylenediaminetetraacetic acid (EDTA), tris(hydroxymethyl)aminomethane (Tris), phosphate buffering agent, N,N-bis(2-hydroxyethyl)glycine (Bicine), N-[tris(hydroxymethyl)-methyl]-3-aminopropanesulfonic acid (Taps), N-2-hydroxyethyl-piperazine-N'-2-hydroxypropane-3-sulfonic acid (Heppso), N-2-hydroxyethyl-piperazine-N'-3-propane-sulfonic acid (Epps), N,N-bis(2-hydroxyethyl)-2-aminoethane sulfonic acid, 3-[N-bis(hydroxyethyl)amino]-2-hydroxypropane-sulfonic acid (Dipso), N-hydroxyethylpiperazine-N'-ethanesulfonic acid (Hepes), piperazine-N,N'-bis(2-hydroxypropanesulfonic acid) dihydrate (Popso), 3-[N-tris(hydroxyethyl)-methylamino]-2-hydroxypropane-sulfonic acid (Tapso), N-tris(hydroxymethyl)-methylaminoethanesulfonic acid (Tes), N-[2-hydroxy-1,1-bis(hydroxymethyl)ethyl]glycine (Tricine) and their alkali metal salts, such as, lithium, sodium and potassium salts and their alkaline earth metal salts. These buffering agents are described in more detail in the literature, such as, Biochemistry, Vol. 5, pp. 467–477 (1986); Analytical Biochemistry, Vol. 104, pp. 300–310 (1980); and Chemical Handbook Fundamental Chapter, pp. 1312–1320, edited by Nippon Chemical Society (published by Maruzen, Tokyo 1966).

Examples of the film-forming hydrophilic polymers which can be used in the reaction layer include the hydrophilic polymers selected from the water-soluble polymer binders which can be used in the indicator layer. Other examples of the hydrophilic polymers which can be used in the reaction layer include gelatin, gelatin derivatives, agarose, pullulan, pullulan derivatives, polyvinyl alcohol and polyacrylamide. Among these polymers, gelatin and gelatin derivatives are preferred.

If desired, the reaction layer may contain wetting agents, binder-crosslinking agents (curing agent), stabilizer, heavy metal ion-trapping agent (a complexing agent) in addition to said reagent capable of reacting with the ammonia-forming substrate to form ammonia, said alkaline buffering agent and said film-forming hydrophilic polymer binder. The heavy metal ion-trapping agent is used to mask heavy metal ions which interfere with the enzyme activity. Examples of the heavy metal ion-trapping agents include complexes, such as, EDTA.2Na, EDTA.4Na, nitrilotriacetic acid (NTA) diethylenetriaminepentaacetic acid.

The reaction layer can be formed by mixing the reagent capable of reacting with the ammonia-forming substrate to form ammonia, said alkaline buffering agent and optionally other reagents stated above with a film-forming hydrophilic binder, such as, gelatin, and applying the resulting coating solution to the surface of the barrier layer or a tacky intermediate layer and drying it.

The reagent capable of reacting with the ammonia-forming substrate to form ammonia is used in an amount of from about 0.1 to 50% by weight, preferably from about 2 to 20% by weight based on the amount of the binder. The alkaline buffering agent is used in an amount of 0.1 to 10% weight on the amount of the binder. The heavy metal ion-trapping agent is used in an amount of about 0.5 to 20% by weight based on the amount of the binder. The dry thickness of the reaction layer is in the range of 1 to 20 $\mu$m, preferably from 3 to 10 $\mu$m.

The tacky intermediate layer which may be provided between the barrier layer and the reaction layer is a layer comprising a polymer composition which is tacky in the air at an ambient temperature (about 0° to about 40° C.) and at a humidity of 10 to 85%. The tacky intermediate layer can be provided by using materials and a method described in Japanese Patent application No. 58(1983)-128759. The polymer composition constituting the tacky intermediate layer is a known polymer having a glass transition point (Tg) of 0° C. or lower, a mixture of such polymers or a mixture of such a polymer or polymers with a conventional tackifier or surfactant. The thickness of the intermediate layer is in the range of about 0.1 to 6 $\mu$m, preferably about 1 to 4 $\mu$m.

Examples of the polymers employable for the preparation of the intermediate layer include a vinyl acetate-butyl acrylate copolymer, polyethyl acrylate, a styrene-butyl acrylate-acrylic acid-N-(hydroxy-methyl)acrylamide quaternary polymer and a butyl acrylate-(ethyl acetoacetate)methacrylate-2-acrylamide-2-methylpropanesulfonic acid ternary polymer.

It is desirable to provide the tacky intermediate layer, when the barrier layer is a polymer barrier layer composed of the homogeneous non-porous thin layer of a hydrophobic (or poorly hydrophilic) polymer.

Directly on the reaction layer or through an intervening layer such as a light-blocking layer described hereinafter, there is provided an intrinsic ammonia-trapping layer containing a reagent which acts on intrinsic ammonia to change it into a form which can not reach said reaction layer. The intrinsic ammonia-trapping layer is a layer capable of trapping the coexisting intrinsic ammonia, before an ammonia-forming substrate, such as, creatinine or urea nitrogen (analyte) reaches the reaction layer and an ammonia-forming reaction takes place.

The term "trapping of intrinsic ammonia" used herein means that the reagent contained in the intrinsic ammonia-trapping layer is bonded to the intrinsic ammonia to bring it into a form which can not be dissociated within analytical operation time, or that the reagent is chemically reacted with the intrinsic ammonia to convert it into other chemical substances (e.g., ammonia salt, ammonium ion or a chemical substance other than gaseous ammonia), whereby the intrinsic ammonia is fixed within the trapping layer to prevent it from reaching the reaction layer. It is preferred that the intrinsic ammonia-trapping layer contains the latter reagent capable of reacting with intrinsic ammonia to fix it. The reagent capable of reacting with the intrinsic ammonia to convert it into other chemical substance hereinafter is referred to as an intrinsic ammonia-trapping reagent.

As such intrinsic ammonia-trapping reagent, preferred is a reagent composition containing an enzyme and having a catalytic performance capable of converting ammonia as a substrate into other substance.

An example of the intrinsic ammonia-trapping reagent includes a reagent composition containing NADH (nicotinamide adenine dinucleotide of reduced type) and/or NADPH (nicotinamide adenine dinucleotide phosphate of the reduced type), glutamate dehydrogenase (EC 1.4.1.3; hereinafter referred to as GLDH) and $\alpha$-ketoglutaric acid (or the salt; hereinafter referred to as α-KG). A reagent composition containing aspartase (EC 4.3.1.1) and fumaric acid or a fumarate may be used. It is preferred to use a reagent composition containing NADH, GLDH and α-KG as the intrinsic ammonia-trapping agent in the analytical element of the present invention. When a reagent composition containing GLDH or a reagent composition containing aspartase is used, it is desirable to use a suitable buffering agent so as to keep the intrinsic ammonia-trapping layer at a pH of 8.5 or below, preferably from 7.0 to 8.5.

Examples of such buffering agents which can be used to keep the pH value in the intrinsic ammonia-trapping reagent include those described in the literature such as, the Chemical Handbook Fundamental Chapter, pp. 1312–1320, edited by Nippon Chemical Society (published by Maruzen, Tokyo 1966); Norman E. Good et al., Biochemistry, 5 (2), 467–477 (1966), Hydrogen Ion Buffers for biological Research, R. M. C. Dawson et al., Data for Biochemical Research, the second edition pp. 476–508 (published by Oxford at the Clarendon Press. 1969) and Analytical Biochemistry, 104, 300–310 (1980). Other examples of the buffering agents include organic acids and alkali metal salt and alkaline earth metal salts used in the analytical element described in Japanese Patent Publication No. 57(1982)-28277 and basic polymers, acidic polymers, the alkali metal or alkaline earth metal salts of the acidic polymers and mixtures thereof used in the analytical element described in Japanese Patent Provisional Publication Nos. 59(1984)-143959 and 60(1985)-10171.

Among these pH buffering agents, particularly preferred examples of the buffering agents are a combination of sodium dihydrogenphosphate, 3-morpholinopropanesulfonic acid (MOPS, CAS Reg. No. [1132-61-2]) and sodium hydroxide, a combination of potassium dihydrogenphosphate and sodium dihydrogenphosphate, a combination of sodium dihydrogenphosphate and citric acid, a combination of boric acid, sodium chloride and borax and a combination of potassium dihydrogenphosphate and sodium tetraborate.

The intrinsic ammonia-trapping layer comprises said intrinsic ammonia-trapping reagent, said pH buffering agent and a film-forming hydrophilic polymer binder. As the hydrophilic polymer binder, there can be used the same hydrophilic polymer binders as those used in the aforementioned reaction layer. Among them, gelatin and gelatin derivatives are preferred.

The thickness of the intrinsic ammonia-trapping layer is in the range of about 1 to 20 μm, preferably about 20 to 10 μm.

It is preferred that the intrinsic ammonia-trapping layer which is a peculiar structural element of the analytical element of the present invention contains NADPH or NADH, α-ketoglutaric acid (α-KG) and glutamate dehydrogenase (GLDH). A particularly preferred content (per $m^2$ of intrinsic ammonia-trapping layer) of each of these ingredients and standard value are shown in the following Table.

|  | Standard value (/$m^2$) | Preferred range (/$m^2$) |
|---|---|---|
| NADPH or NADH | 160 mg. | 80–1300 mg. |
| α-KG | 1800 mg. | 400–8000 mg. |
| GLDH | 17000 units | 2000–70000 units |

Accordingly, it is preferred that the intrinsic ammonia-trapping layer contains at least 80 mg./$m^2$ of NADPH and/or NADH, at least 400 mg./$m^2$ of α-ketoglutaric acid and least 2000 units/$m^2$ of glutaric dehydrogenase.

When the intrinsic ammonia-trapping layer contains aspartase and fumaric acid or a fumarate, the preferred content of aspartase is at least 1000 units/$m^2$ and that of fumaric acid (and/or fumarate) is at least 200 mg./$m^2$.

There may also be provided a light-blocking layer between the barrier layer and the intrinsic ammonia-trapping layer. The light-blocking layer is a water-permeable layer in which light-blocking (or light-reflecting) fine particles are dispersed in small amount of a film-forming hydrophilic (or weakly hydrophilic) polymer binder. The light-blocking layer may function as light-reflecting layer or background layer as well as a blocker to the color of an aqueous liquid spotted on the spreading layer, such as, the red of hemoglobin in a whole blood sample, when a detectable change (a color change or a color development etc.) in the indicator layer is measured from the side of the transparent support by reflection photometry.

Examples of light-blocking and light-reflecting particles include titanium dioxide fine particles, barium sulfate fine particles, aluminum fine particles and fine flakes thereof. Examples of light-blocking particle include carbon black, gas black and carbon microbeads. Most preferred are titanium dioxide fine particles and barium sulfate fine particles.

Examples of the film-forming hydrophilic (or weakly hydrophilic) polymer binders include gelatin (e.g., acid-treated gelatin, deionized gelatin), gelatin derivatives (e.g., phthalinized gelatin and hydroxymethyl acrylate-grafted gelatin), polyvinyl alcohol, regenerated cellulose and cellulose acetate (e.g. cellulose diacetate), among which gelatin, gelatin derivatives and polyacrylamide are preferred. Gelatin and gelatin derivative can be used together with a conventional curing agent (cross-linking agent) as a mixture.

The ratio of the polymer binder to the light-blocking fine particle is in the range from about 2.5 to 7.5, preferably from about 3.0 to 6.5 of the polymer binder to 10 of the particle on a dry volume basis. When the light-blocking fine particle is fine titanium dioxide particle, the ratio is in the range from about 0.6 to 1.8, preferably from 0.8 to 1.5 of the polymer binder to 10 of the particle on a dry weight basis. The dry thickness of the light-blocking layer is in the range from 3 μm to 30 μm, preferably about 5 μm to 20 μm.

The light-blocking layer can be provided in such a manner that an aqueous dispersion containing the light-blocking particle and the hydrophilic polymer (optionally, further other reagents such as surfactant) is coated on the barrier layer and then dried by any of the conventional methods. The light-blocking layer may be provided between the intrinsic ammonia-trapping layer and a porous spreading layer described hereinafter instead of providing between the intrinsic ammonia-trapping layer and the barrier layer. Alternatively, the light-blocking particles may be incorporating in the spreading layer instead of providing the light-blocking layer.

There may also be provided an adhesive layer on the intrinsic ammonia-trapping layer or the optionally added other layer (e.g., light-blocking layer) to enhance the adhesion of the spreading layer.

The adhesive layer is preferably composed of a hydrophilic polymer which can bond the spreading layer to the other layer to make all of the layers integrated while the polymer is wetted or swelled with water.

Examples of the hydrophilic polymer include the polymers employable in the reaction layer. Most preferred are gelatin, gelatin derivatives and polyacrylamide. The dry thickness of the adhesive layer generally ranges from approx. 0.5 $\mu$m to approx. 20 $\mu$m, preferably from approx. 1 $\mu$m to approx. 10 $\mu$m.

The adhesive layer can be prepared in such a manner that a solution of a hydrophilic polymer and optionally added other agent such as a surfactant is coated on the intrinsic ammonia-trapping layer or other layer.

A porous spreading layer (hereinafter referred to as spreading layer) is provided on the layer. The spreading layer preferably has a metering effect (i.e., metering the spotted liquid sample). The term "spreading layer capable of metering a liquid sample" herein used refers to a layer having a function capable of spreading an applied liquid in the form of circle in such a manner that the spread area of the liquid is approximately in proportion to the amount of the liquid when the liquid is applied thereon and further having a function capable of supplying the liquid to the intrinsic ammonia-trapping layer.

Examples of materials constituting the matrix of the porous spreading layer of the integral multilayer analytical element include filter paper, nonwaven fabric, woven fabric, knitted fabric, glass fiber, membrane filter and the three-dimentional lattice structure composed of the microbead of a polymer.

The matrix of the spreading layer is chosen from the above-described materials according to the analytical conditions. When the sample containing insoluble materials which are inhibitors to the analysis (e.g., whole blood containing blood cell) is applied, the woven fabric and the knitted fabric which function to eliminate such inhibitors are most advantageous.

Examples of the woven fabrics (woven cloth) which can be used for the porous reagent layer include those disclosed in Japanese Patent Provisional Publications No. 55(1980)-164356 and No. 57(1982)-66359. Among the woven fabrics, plain weave fabrics made of warp and weft are preferred. Among plain woven fabrics, thin cloth, muslin, broadcloth and poplin are preferred.

Examples of yarns for woven cloth include those composed of the same materials as those constituting knitted cloths as described in more detail hereinafter. Any of filament yarn and spun yarn (twist yarn) can be used, and the spun yarn is preferred. The yarn diameter of the woven fabric is generally in the range of about 20S to about 150S, preferably about 40S to about 120S in terms of cotton spinning yarn count or in the range of about 35 to about 300D, preferably about 45 to about 130D in terms of silk thread denier. The thickness of the woven fabric is generally in the range of about 100 to about 500 $\mu$m, preferably about 120 to 350 $\mu$m. The voids of the woven fabric are generally in the range of about 40 to about 90%, preferably about 50 to about 85%.

Examples of the knitted fabrics which can be used for the porous reagent layer include many kinds of knitted fabrics, among which warp knitted fabric and weft knitted fabric are preferred. Examples of the warp knitted fabrics include single atlas knitted cloth, tricot knitted cloth, double tricot knitted cloth, milanese knitted cloth and rashar knitted cloth. Examples of the weft knitted fabrics include plain weave knitted cloth, pearl knitted cloth, rib stitch cloth, and double face knitted cloth. Examples of the yarns for knitted fabrics include yarns of natural fibers such as cotton, silk and wool; yarns composed of fine fibers or single fibers of regenerated cellulose (e.g. viscose rayon and cupra), semi-synthetic organic polymer (e.g. cellulose diacetate and cellulose triacetate), synthetic organic polymer (e.g., polyamide such as nylon, acetalated polyvinyl alcohol such as vinylon, polyacrylonitrile, polyethylene terephthalate, polyethylene, polypropylene and polyurethane), and yarns composed of fiber blends of a natural fiber and a regenerated cellulose or a semi-synthetic or synthetic organic polymer fiber. Any of filament yarn and spun yarn can be used, and spun yarn is preferred. The diameter of the yarn for knitted fabric is generally in the range of from about 40 to 150S, preferably about 60 to about 120S in terms of cotton spinning yarn count, or in the range of about 35 to about 130D, preferably about 45 to about 90D in terms of silk thread denier. The number of knitting gauge of the knitted fabric is generally in the range of about 20 to about 50. The thickness of the knitted fabric is generally in the range of about 100 to about 600 $\mu$m, preferably about 150 to about 400 $\mu$m. The voids of the knitted fabric are generally in the range of about 40 to about 90%, preferably about 50 to about 85%. The warp knitted fabric, tricot knitted cloth, rashar knitted cloth, milanese knitted cloth and double tricot knitted cloth are preferred, because shrinkage in the wale direction is small, the operation in the lamination stage of knitted goods is easy and the stitches are not easily loosened during cutting.

Woven fabric or knitted fabric is preferably a fabric from which grease is substantially removed when the yarn or the fabric is prepared. The fabrics are more preferably processed to be hydrophilic to enhance the adhesion to an underlying layer. Examples of such processes to make the fabric hydrophilic include physical activating processes (preferably a glow discharge process or corona discharge process) disclosed in Japanese Patent Provisional Publication No. 57(1982)-66359 and hydrophilic polymer permeating processes disclosed in Japanese Patent Provisional Publication Nos. 55(1980)-164356 and 57(1982)-66359.

The spreading layer of woven fabric or knitted fabric can be laminated on the intrinsic ammonia-trapping layer, the light-blocking layer or the adhesive layer according to the process disclosed in Japanese Patent Provisional Publications No. 55(1980)-164356 and No. 57(1982)-66359. In this process, woven or knitted fabric is laminated under substantially uniform light pressure on the wet or swollen layer to be laminated which is still in the wet condition after coating or has been supplied with water (or water containing small amount of detergent) after drying.

The spreading layer composed of a membrane filter is disclosed in Japanese Patent Publication No. 53(1978)-21677. The spreading layer composed of a three-dimentional lattice structure composed of the microbeas of a polymer is disclosed in Japanese Patent Provisional Publication No. 55(1980)-90859. The spreading layer constituted of filter paper or nowaven fabric is disclosed in Japanese Patent Provisional Publication No. 57(1982)-148250.

A porous spreading layer having a definite surface may be used as the porous spreading layer. Such a porous spreading layer having a definite surface can be provided by using materials and a method described in Japanese Utility Model Provisional Publication No. 57(1982)-42951 and Japanese Patent Provisional Publication No. 57(1982)-208998.

If desired, the light-blocking particle or reagents such as a surfactant may be incorporated in the spreading layer of the present invention.

The measurement of an ammonia-forming material with the analytical element of the present invention can be made in such a manner that 5 to 30 μm of a sample solution is spotted (deposited) on the spreading layer of the analytical element, the element is incubated at 30° to 40° C., preferably 35° to 39° C. for 1 to 20 minutes, preferably 2 to 10 minutes, and the degree of the color change (color formation, color change or fading) is measured from the side of the support by reflection photometry or the degree of the color change is visually compared with standard color.

The following examples and comparison example are provided to illustrate the present invention without limiting it thereto.

EXAMPLE 1

An ammonia indicator layer (dry thickness: 4 μm) was formed on a transparent polyethylene terephthalate (PET) film (thickness: 180 μm) by coating the film with a coating solution and drying it. A water-repellent membrane filter (Fuji Microfilter FM 120 manufactured by Fuji Photo Film Co., Ltd.; thickness: 140 μm, voids: about 75%, average pore size: 1.2 μm, said filter was immersed in a hexane solution of a water-repellent silicon resin and dried, whereby said filter was made water-repellent) was sticked on said ammonia indicator layer (which was bondable even in the dried state) to form a barrier layer.

Subsequently, a reaction layer (dry thickness: 8 μm), a light-blocking layer (dry thickness: 5 μm), an intrinsic ammonia-trapping layer (dry thickness: 5 μm) and then an adhesive layer (dry thickness: 5 μm) in this order are formed on said barrier layer by coating each coating solution and drying it in order.

The surface coated with the above-described layers in the dried state was swollen with water, and a cloth (No. 100 count cotton broadcloth) as a spreading layer was laminated onto said wetted surface under pressure, thus preparing an integral multilayer analytical element for use in the analysis of creatinine.

The composition and the preparation of each coating solution for the formation of the ammonia indicator layer, the light-blocking layer, the intrinsic ammonia-trapping layer and the adhesive layer were as follows (the amount of the coating composition being a coated amount per m² of each layer).

Coating Solution for Ammonia Indicator Layer

| Bromophenol Blue | 0.7 g. |
|---|---|
| Ethanol - water | 20 ml |
| Polyvinyl acetate - acrylate ester copolymer latex binder (solid content: about 50%, pH: 4.5) | 15 g. |
| Polyoxyethylene nonylphenyl ether | 0.15 g. |
| Water | 40 g. |

The pH of the coating solution having the above composition was adjusted to 2.60 with citric acid.

Coating Solution for Reaction Layer

| Gelatin | 15 g. |
|---|---|
| Water | 128 g. |
| p-Nonylphenoxy polyglycidol | 0.3 g. |

-continued

| Tetrasodium ethylenediaminetetraacetate | 0.3 g. |
|---|---|
| Disodium hydrogenphosphate | 0.2 g. |
| Taps[(N-tris(hydroxymethyl)methyl-3-aminopropanesulfonic acid] | 3 g. |
| Tris[(tris(hydroxymethyl)aminomethane)] | 3 g. |
| Creatinine iminohydrolases | 3500 units |

The pH of the coating solution having the above composition was adjusted to 9.2 with sodium hydroxide.

Coating Solution for Light-blocking Layer

| Fine titanium dioxide powder | 4 g. |
|---|---|
| Gelatin | 4 g. |
| p-Nonylphenoxy polyglycidol | 0.2 g. |
| Water | 42 g. |

Coating Solution for intrinsic Ammonia-Trapping Layer

| Gelatin | 5 g. |
|---|---|
| Water | 40 g. |
| p-Nonylphenoxy polyglycidol | 0.2 g. |
| α-Ketoglutaric acid | 800 mg. |
| NADPH | 160 mg. |
| Glutamate dehydrogenase | 7500 units |
| Potassium dihydrogenphosphate | 0.3 g. |

The pH of the coating solution having the above composition was adjusted to 8.0 with $Na_2B_4O_7$.

Coating Solution for Adhesive Layer

| Gelatin | 5 g. |
|---|---|
| Water | 60 g. |
| p-Nonylphenoxy polyglycidol | 0.2 g. |

COMPARISON EXAMPLE 1

The procedure of Example 1 was repeated except that the intrinsic ammonia-trapping layer was omitted to prepare an analytical element for the purpose of comparison.

The analytical element obtained by Example 1 according to the present invention and the analytical element obtained by Comparison Example 1 were evaluated and compared with each other in the following manner.

A 7% aqueous albumin solution (blank), a 7% aqueous albumin solution containing 400 μg/dl of ammonium sulfate as ammonia nitrogen and a 7% aqueous albumin solution containing creatinine at a concentration of 1, 4, 8 or 20 mg./dl were prepared. Further, a 7% aqueous albumin solution containing ammonium sulfate (400 μg/dl) and creatinine at a concentration of 1, 4, 8 or 20 mg./dl was prepared. 10 μl of each of these solutions was dropped on the spreading layer of each of the analytical elements of Example 1 and comparison Example 1. The analytical elements were then incubated at 37° C. for 6 mins., and the color density of each element was measured with a light of 600 nm by reflection photometry. The results are shown in Table 1 wherein $NH_4^+$ means ammonium sulfate.

TABLE 1

| Test Solution (7% aq. albumin solution) | Optical Reflection Density Ex. 1 | Comp. Ex. 1 |
|---|---|---|
| (blank) | 0.350 | 0.352 |
| $NH_4^+$ 400 μg./dl | 0.355 | 0.470 |
| creatinine 1 mg./dl | 0.385 | 0.390 |
| creatinine 4 mg./dl | 0.460 | 0.472 |
| creatinine 8 mg./dl | 0.530 | 0.543 |
| creatinine 20 mg./dl | 0.800 | 0.815 |
| creatinine 1 mg./dl + $NH_4^+$ 400 μg./dl | 0.387 | 0.535 |
| creatinine 4 mg./dl + $NH_4^+$ 400 μg./dl | 0.465 | 0.610 |
| creatinine 8 mg./dl + $NH_4^+$ 400 μg./dl | 0.540 | 0.675 |
| creatinine 20 mg./dl + $NH_4^+$ 400 μg./dl | 0.813 | 0.960 |

It is apparent from the above result that the analytical element of comparison Example 1 having no intrinsic ammonia-trapping layer is affected by intrinsic ammonia, while the analytical element of Example 1 having the intrinsic ammonia-trapping layer is not affected by intrinsic ammonia (see, the line of $NH^+_4$ 400 μm/dl).

EXAMPLE 2

An ammonia indicator layer (dry thickness: 4 μm) was formed on a transparent polyethylene terephthalate (PET) film (thickness: 180 μm) by coating the film with a coating solution and drying it. A water-repellent membrane filter (Fuji Microfilter FM 300, thickness: 140 μm, voids: about 75%, average pore size: 1.2 μm, said filter was immersed in a hexane solution of a water-repellent silicon resin and dried, whereby the film was made water-repellent) was stuck on said indicator layer (which was tacky even in the dried state) to form a barrier layer.

Subsequently, a reaction layer (dry thickness: 8 μm), a light-blocking layer (dry thickness: 5 μm), an intrinsic ammonia-trapping layer (dry thickness: 5 μm) and an adhesive layer (dry thickness: 5 μm) in this order were formed on said barrier by coating each coating solution and drying it.

The surface coated with the above-described layers in the dried state was swelled with water, and a cloth (No. 100 count cotton broadcloth) as a spreading layer were laminated onto said wetted surface to prepare an integral multilayer analytical element for the analysis of creatinine.

The composition and the preparation of each of the coating solutions for the formation of the indicator layer, the reaction layer, the light-blocking layer, the intrinsic ammonia-trapping layer and the adhesive layer were as follows (the amount of the composition being the coated amount per m² of each layer).

Coating Solution for Indicator Layer

| Bromophenol Blue | 0.7 g. |
|---|---|
| Ethanol - water | 7.5 ml |
| Polyvinyl acetate - acrylate ester copolymer latex binder (solid content: about 50%, pH: 4.5) | 15 g. |
| Polyoxyethylene nonylphenyl ether | 0.15 g. |
| Water | 40 g. |

The pH of the coating solution having the above composition was adjusted to 2.60 with citric acid.

Coating Solution for Reaction Layer

| Gelatin | 15 g. |
|---|---|
| Water | 128 g. |
| p-Nonylphenoxy polyglycidol | 0.3 g. |
| Tetrasodium ethylenediaminetetraacetate | 0.3 g. |
| Disodium hydrogenphosphate | 0.2 g. |
| Taps[(N-tris(hydroxymethyl)methyl-3-aminopropanesulfonic acid] | 3 g. |
| Tris[(tris(hydroxymethyl)aminomethane)] | 3 g. |
| Creatinine iminohydrolases | 4400 units |

The pH of the coating solution having the above composition was adjusted to 9.5 with sodium hydroxide.

Coating Solution for Light-blocking Layer

| Fine titanium dioxide powder | 4 g. |
|---|---|
| Gelatin | 6 g. |
| p-Nonylphenoxy polyglycidol | 0.2 g. |
| Water | 60 g. |

Coating Solution for Intrinsic Ammonia-trapping Layer

| Gelatin | 5 g. |
|---|---|
| Water | 40 g. |
| p-Nonylphenoxy polyglycidol | 0.2 g. |
| α-Ketoglutaric acid | 800 mg. |
| NADH | 160 mg. |
| Glutamate dehydrogenase | 7500 units |
| Potassium dihydrogenphosphate | 0.1 g. |
| MOPS[3-(N-morpholino)propanesulfonic acid] | 0.5 g. |

The pH of the coating solution having the above composition was adjusted to 8.0 with NaOH.

Coating Solution for Adhesive Layer

| Gelatin | 5 g. |
|---|---|
| Water | 60 g. |
| p-Nonylphenoxy polyglycidol | 0.2 g. |

COMPARISON EXAMPLE 2

The procedure of Example 2 was repeated except that the intrinsic ammonia-trapping layer was omitted to prepare an analytical element for the purpose of comparison.

The analytical element of the present invention and that of Comparison Example were evaluated and compared with each other in a similar manner to that described above. The results are shown in Table 2.

TABLE 2

| Test Solution (7% aq. albumin solution) | Optical Reflection Density Ex. 2 | Comp. Ex. 2 |
|---|---|---|
| (blank) | 0.405 | 0.410 |
| $NH_4^+$ 200 μg./dl | 0.410 | 0.480 |
| creatinine 1 mg./dl + $NH_4^+$ 200 μg./dl | 0.440 | 0.515 |
| creatinine 4 mg./dl + $NH_4^+$ 200 μg./dl | 0.520 | 0.585 |
| creatinine 8 mg./dl + $NH_4^+$ 200 μg./dl | 0.590 | 0.672 |
| creatinine 20 mg./dl + $NH_4^+$ 200 μg./dl | 0.860 | 0.935 |

It is apparent from the above results that the analytical element of Comparison Example 2 having no intrinsic ammonia-trapping layer is affected by intrinsic ammonia, while the analytical element of Example 2 having the intrinsic ammonia-trapping layer is not affected by intrinsic ammonia (see, line of $NH_4^+$ 200 μg./dl).

We claim:

1. An integral multilayer analytical element for the analysis of an ammonia-forming substrate in a liquid sample containing intrinsic ammonia comprising:
   (I) a light-transmissive, liquid-impermeable support;
   (II) an ammonia indicator layer containing a reagent capable of undergoing a detectable change by gaseous ammonia;
   (III) a liquid barrier layer which allows gaseous ammonia passing therethrough;
   (IV) an ammonia-forming substrate reaction layer containing a reagent capable of reacting with an ammonia-forming substrate to form gaseous ammonia;
   (V) an intrinsic ammonia trapping layer having a thickness in the range of 1 to 20 μm and containing a buffering reagent therein to keep its pH value in the range of from 7.0 to 8.5 and containing a combination of NADH or NADPH, α-ketoglutaric acid and glutamate dehydrogenase to chemically react with the intrinsic ammonia to convert it into other chemical substance so that the intrinsic ammonia is fixed therein and kept from reaching said reaction layer;
   (VI) a porous spreading layer, in a laminate form in this order with the proviso that said (I) is the lowest member and said (VI) is the uppermost layer.

2. The integral multilayer analytical element as claimed in claim 1, wherein said intrinsic ammonia-trapping layer contains NADH and/or NADPH in an amount of at least 80 mg./m$^2$, α-ketoglutaric acid in an amount of at least 400 mg./m$^2$ and glutamate dehydrogenase in an amount of at least 2,000 units/m$^2$.

3. The integral multilayer analytical element as claimed in claim 1, wherein said reaction layer contains an enzyme capable of reacting with creatinine to form ammonia.

4. The integral multilayer analytical element as claimed in claim 1, wherein a light-blocking layer is interposed between the ammonia-forming substrate reaction layer and the intrinsic ammonia trapping layer.

5. An integral multilayer analytical element for the analysis of an ammonia-forming substrate in a liquid sample containing intrinsic ammonia comprising:
   (I) a light-transmissive, liquid-impermeable support;
   (II) an ammonia indicator layer containing a reagent capable of undergoing a detectable change by gaseous ammonia;
   (III) a liquid barrier layer which allows gaseous ammonia passing therethrough;
   (IV) an ammonia-forming substrate reaction layer containing a reagent capable of reacting with an ammonia-forming substrate to form gaseous ammonia;
   (V) an intrinsic ammonia trapping layer having a thickness in the range of 1 to 20 μm, containing a buffering reagent therein to keep its pH value in the range of from 7.0 to 8.5 and containing a combination of aspartase and fumaric acid or fumarate to chemically react with the intrinsic ammonia to convert it into another chemical substance so that the intrinsic ammonia is fixed therein and kept from reaching said reaction layer;
   (VI) a porous spreading layer, in a laminate form in this order with the proviso that said (I) is the lowest member and said (VI) is the uppermost layer.

6. The integral multilayer analytical element as claimed in claim 5, wherein said intrinsic ammonia-trapping layer contains aspartase and fumaric acid.

7. The integral multilayer analytical element as claimed in claim 5, wherein said intrinsic ammonia-trapping layer contains asparatase in an amount of at least 1,000 units/m$^2$ and fumaric acid or fumarate in an amount of at least of 200 mg/m$^2$.

* * * * *